United States Patent
Kadykowski

(10) Patent No.: US 9,282,952 B2
(45) Date of Patent: Mar. 15, 2016

(54) INTERNAL PRESERVATION FLUID DISPENSER FOR ENDOSCOPIC VESSEL HARVESTER

(71) Applicant: Terumo Cardiovascular Systems Corporation, Ann Arbor, MI (US)

(72) Inventor: Randal J. Kadykowski, South Lyon, MI (US)

(73) Assignee: TERUMO CARDIOVASCULAR SYSTEMS CORP., Ann Arbor, MI (US)

( * ) Notice: Subject to any disclaimer, the term of this patent is extended or adjusted under 35 U.S.C. 154(b) by 305 days.

(21) Appl. No.: 14/064,750

(22) Filed: Oct. 28, 2013

(65) Prior Publication Data

US 2015/0119917 A1    Apr. 30, 2015

(51) Int. Cl.
A61B 17/22 (2006.01)
A61B 17/00 (2006.01)
A61B 17/32 (2006.01)
A61B 18/14 (2006.01)
A61B 18/00 (2006.01)

(52) U.S. Cl.
CPC ... *A61B 17/00008* (2013.01); *A61B 17/320016* (2013.01); *A61B 18/1482* (2013.01); *A61B 2017/00969* (2013.01); *A61B 2018/00029* (2013.01); *A61B 2018/00601* (2013.01); *A61B 2217/007* (2013.01); *A61B 2218/003* (2013.01)

(58) Field of Classification Search
CPC .............. A61B 2017/320084; A61B 17/00008; A61B 2218/002; A61B 2218/003; A61B 2217/007; A61B 17/320016; A61B 2017/320028; A61B 17/320068; A61B 2017/320072; A61B 17/320088
See application file for complete search history.

(56) References Cited

U.S. PATENT DOCUMENTS

| | | | |
|---|---|---|---|
| 5,928,138 A * | 7/1999 | Knight ............ | A61B 17/00008 600/104 |
| 5,970,982 A | 10/1999 | Perkins | |
| 7,442,192 B2 | 10/2008 | Knowlton | |
| 7,547,314 B2 | 6/2009 | Kadykowski | |
| 7,708,735 B2 | 5/2010 | Chapman et al. | |
| 7,850,687 B2 | 12/2010 | Kasahara | |
| 8,123,672 B2 | 2/2012 | Viitala et al. | |
| 8,303,594 B2 * | 11/2012 | Lynch ................. | A61B 17/1668 606/170 |
| 8,465,488 B2 * | 6/2013 | Maeda ................ | A61B 18/148 606/46 |
| 8,657,818 B2 * | 2/2014 | Lin .................. | A61B 17/00008 606/170 |
| 2003/0065326 A1 * | 4/2003 | Wellman ............ | A61B 18/1482 606/50 |
| 2003/0130674 A1 * | 7/2003 | Kasahara .......... | A61B 17/00008 606/159 |
| 2004/0049208 A1 | 3/2004 | Hill et al. | |
| 2005/0159764 A1 * | 7/2005 | Kasahara .......... | A61B 17/00008 606/159 |
| 2006/0241665 A1 * | 10/2006 | Bosley ........... | A61B 17/320016 606/167 |
| 2007/0185481 A1 * | 8/2007 | Kasahara ........... | A61B 17/3421 606/37 |
| 2011/0046439 A1 * | 2/2011 | Pamnani ............. | A61B 1/018 600/104 |

* cited by examiner

*Primary Examiner* — Jonathan W Miles
(74) *Attorney, Agent, or Firm* — Gael Diane Tisack, Esq.; Darryl Newell; MacMillan, Sobanski & Todd

(57) ABSTRACT

An endoscopic vessel harvester includes a vessel keeper for capturing a target vessel within a tunnel that has been dissected along the target vessel. A cutter member cuts and cauterizes side branches while the target vessel is slidably captured in the vessel keeper. A spray nozzle carried by the vessel keeper delivers a preservative fluid via a manual control valve and a conduit. The preservative fluid is sprayed on the target vessel proximate a respective side branch immediately after being cauterized. Thus, a harvested vessel is bathed in preservative fluid prior to being actually removed from the body, enhancing endothelial preservation from cascading events.

6 Claims, 3 Drawing Sheets

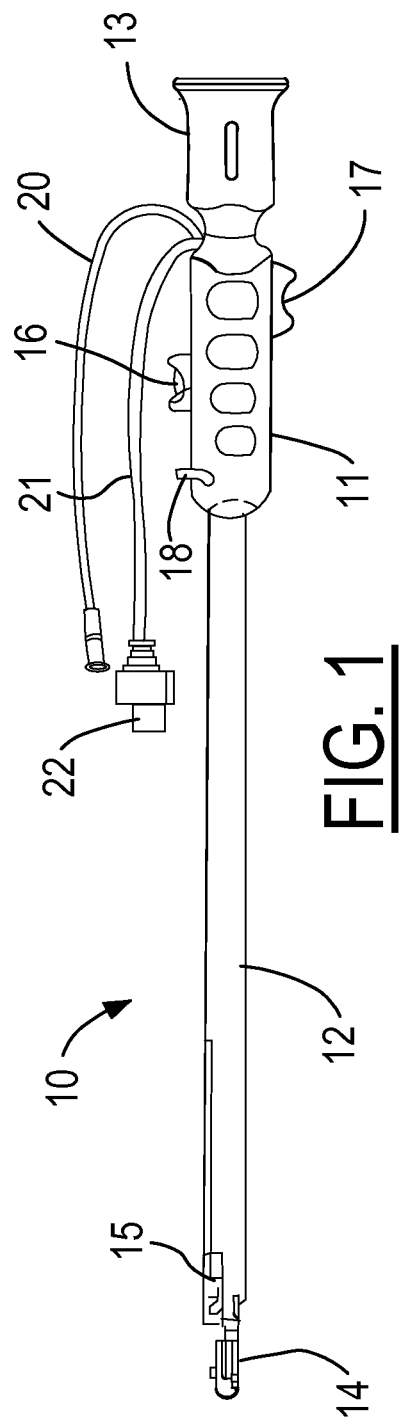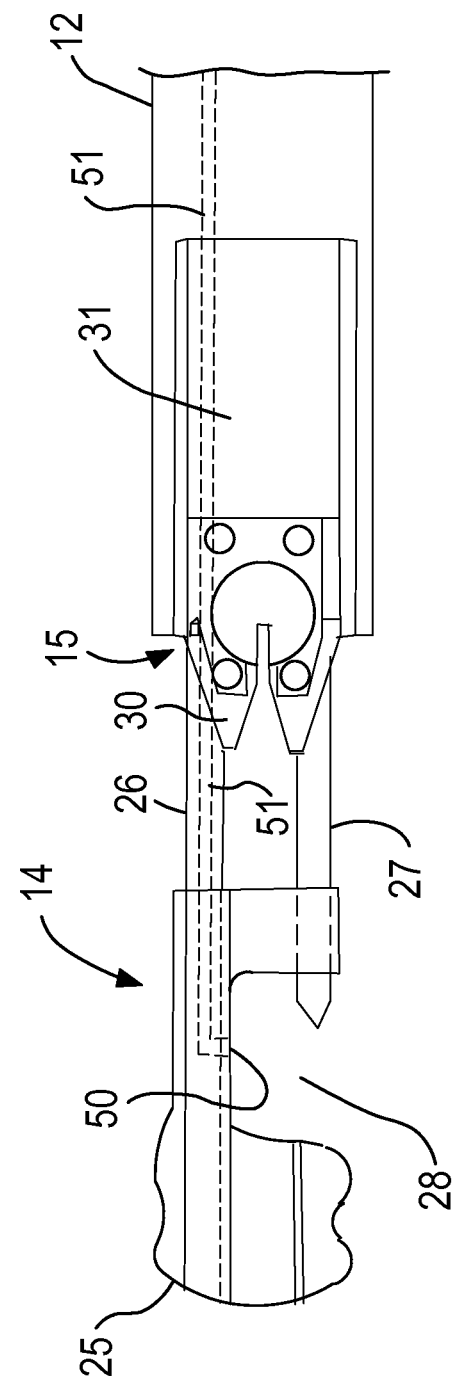

INTERNAL PRESERVATION FLUID DISPENSER FOR ENDOSCOPIC VESSEL HARVESTER

CROSS REFERENCE TO RELATED APPLICATIONS

Not Applicable.

STATEMENT REGARDING FEDERALLY SPONSORED RESEARCH

Not Applicable.

BACKGROUND OF THE INVENTION

The present invention relates in general to endoscopic harvesting of blood vessels, and, more specifically, to reducing endothelial damage resulting from dissection, cauterizing, and handling of a target vessel.

In coronary artery bypass grafting (CABG), a blood vessel or vessel section, such as an artery or vein, is "harvested" (i.e., removed) from its natural location in a patient's body for use as a graft. After removal, the section of blood vessel is joined between an arterial blood source and the coronary artery that is to be bypassed. Among the preferred sources for the vessel to be used as the bypass graft are the saphenous vein in the legs and the radial artery in the arms.

Endoscopic surgical procedures for harvesting a section of a vessel (e.g., the saphenous vein) subcutaneously have been developed in order to avoid disadvantages and potential complications of older harvesting techniques wherein a continuous incision (e.g., along the leg) was made for the full length of the desired vessel section in order to provide adequate exposure for visualizing the vessel and for introducing surgical instruments to sever, cauterize, and ligate the tissue and side branches of the vessel. One such minimally-invasive technique employs a small incision for locating the desired vessel and for introducing one or more endoscopic harvesting devices. Primary dissection occurs by introduction of a dissecting instrument through the incision to create a working space and to separate the vessel from the surrounding tissue. Then a cutting instrument is introduced into the working space to sever the blood vessel from the connective tissue surrounding the section to be harvested and any side branches of the blood vessel. The branches may be clipped and/or cauterized.

In one typical procedure, the endoscopic entry site is located near the midpoint of the vessel being harvested, with dissection and cutting of branches proceeding in both directions along the vessel from the entry site. In order to remove the desired section of the blood vessel, a second small incision, or stab wound, is made at one end thereof and the blood vessel section is ligated. A third small incision is made at the other end of the blood vessel section which is then ligated, thereby allowing the desired vessel section to be completely removed through the first incision. Alternatively, only the first two incisions may be necessary if the length of the endoscopic device is sufficient to obtain the desired length of the blood vessel while working in only one direction along the vessel from the entry point.

An example of a commercially available product for performing the endoscopic vessel harvesting described above is the VirtuoSaph™ Endoscopic Vein Harvesting System from Terumo Cardiovascular Systems Corporation of Ann Arbor, Mich. Endoscopic vessel harvesting systems are described in U.S. Pat. No. 8,465,488 to Maeda et al and U.S. Pat. No. 7,547,314 to Kadykowski, both of which are incorporated herein by reference in their entirety. After harvesting, the vessel is inspected and prepared for surgery by checking for leaks or other defects. The prepared vessel is then stored in a preservative fluid until needed. U.S. Pat. No. 8,123,672 discloses a kit for preparing and preserving a blood vessel for bypass graft surgery.

In the VirtuoSaph™ System, the cutting tool for severing and cauterizing branches has the form of a V-cutter wherein a V-shaped tip at the distal end of the cutter guides a branch to be cut into a longitudinal slit. Electrodes adjacent the slit are electrically energized with a high frequency voltage in order to cauterize and sever the branch by coagulation. Unfortunately, a cascade of biochemical events within the tissue can affect the endothelium. It would be advantageous if the cascade of events could be minimized with respect to the endothelium in order to improve the long term patency of vessels used as coronary artery bypass grafts.

SUMMARY OF THE INVENTION

In one aspect of the invention, an endoscopic vessel harvester comprises a longitudinal insertion member having a proximal end with a handle and a distal end adapted for insertion into a tunnel dissected along a target vessel within a body of a patient. A vessel keeper is extendably mounted at the distal end of the insertion member comprising a capture frame with a movable side having an opened position to admit the target vessel and having a closed position to slidably capture the target vessel. A cutter member is extendably mounted at the distal end of the insertion member having a cauterizing element adapted to contact side branches of the target vessel and to cut and cauterize the side branches while the target vessel is slidably captured in the vessel keeper. A spray nozzle is carried by the vessel keeper. A preservative distributor includes a manual control valve and a conduit between the valve and the spray nozzle adapted to deliver a preservative fluid to the target vessel proximate a respective side branch immediately after being cauterized. Thus, a harvested vessel is bathed in preservative fluid prior to being actually removed from the body, lessening endothelial damage arising from cascading biochemical events.

BRIEF DESCRIPTION OF THE DRAWINGS

FIG. 1 is a side view of a vessel harvester of the invention.

FIG. 2 is a top view of the distal end of the vessel harvester.

DETAILED DESCRIPTION OF PREFERRED EMBODIMENTS

Figure 3:
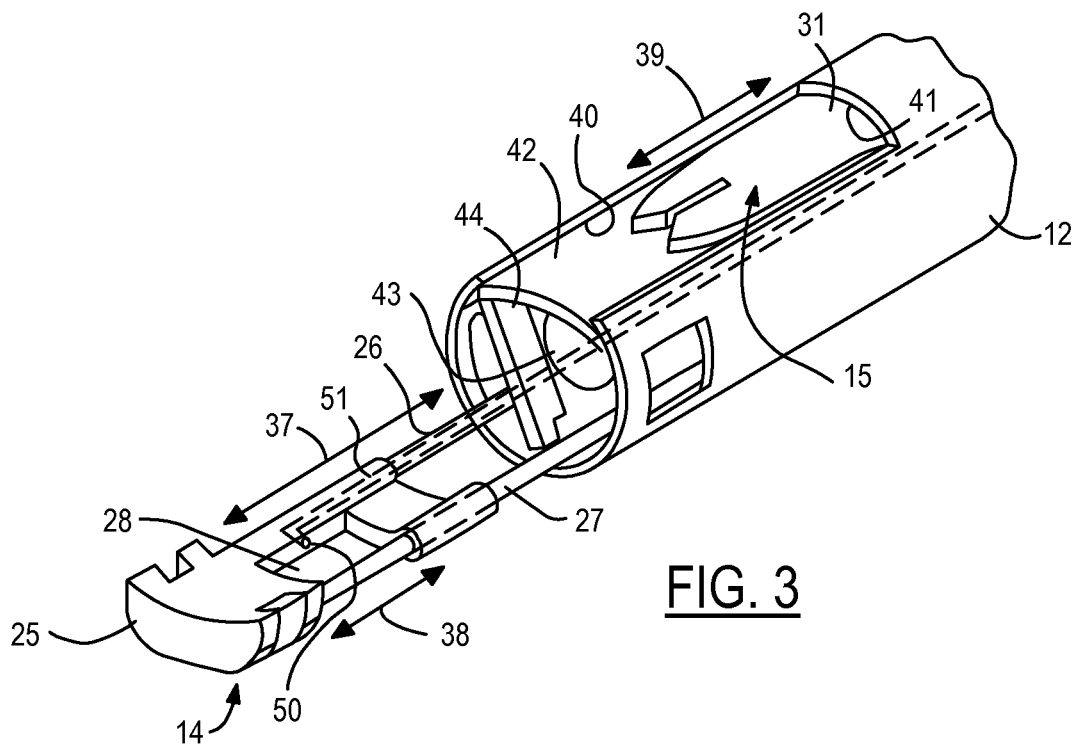
FIG. 3 is a perspective view of the distal end of the harvester.

FIG. 1 shows a harvester rod 10 used to grasp the target vessel being dissected and to sever any branches or connective tissue connecting to the vessel. Harvester rod 10 is inserted into a working tunnel along a target vessel that is created using a dissector rod (not shown). Harvester rod 10 has a handle 11 connected to an elongated sleeve member or insertion member 12 and to an endoscope receiver 13. At the distal end of insertion member 12 are a vessel-keeper (V-keeper) 14 which is a capture frame for retaining the vessel being dissected and a V-cutter 15 for severing side branches and connective tissue. V-keeper 14 is manipulated by V-keeper buttons 16 on handle 11. V-cutter 15 is extended or retracted by manipulating a V-cutter extender button 17 on handle 11. An endoscope wiper lever 18 may be provided on handle 11 for controlling a wiper that clears the end of the endoscope when the endoscope optics become covered by material from the body cavity. An insufflator tube 20 can be connected to a source of gas such as $CO_2$ to deliver insufflation gas to the distal end of insert member 12. A bipolar cord 21 has a connector 22 at one end for connecting to a source of high frequency voltage, and includes conductors for supplying the voltage to electrodes on V-cutter 15.

V-keeper 14 and V-cutter 15 are shown in greater detail in FIG. 2. V-keeper 14 includes a guide frame 25 mounted to a support rod 26 and a movable rod 27. Guide frame 25 and rod 27 together form the capture frame with an internal opening 28. The vein or other vessel to be harvested is maneuvered into opening 28, and then the V-keeper buttons on the handle are manipulated to extend rod 27 along one side of the capture frame in order to close opening 28 and thereby retain the vessel. V-cutter 15 includes a V-tip 30 with a central slit mounted to an extendable guide 31 that is manipulated by the V-cutter button on the handle in order to place side branches into the slit.

FIG. 3 shows the distal end of harvester rod 10 in greater detail. V-keeper 14 is longitudinally extendable as shown by arrow 37 while rod 27 is independently longitudinally extendable as shown by arrow 38. In FIG. 3, rod 27 is in an extended position used for maintaining the vessel being harvested within opening 28 (i.e., the side of the capture frame is closed).

V-cutter 15 is longitudinally extendable in the directions shown by arrow 39. Elongated insertion member 12 has a notch 40 with a terminal edge 41 which exposes V-cutter 15 prior to being extended further than the end of insertion member 12. A guard piece 42 is provided beneath V-cutter 15. A lens portion 43 at the end of the endoscope is shown positioned near the distal end of member 12. A wiper 44 is mounted for pivoting over lens 43 as controlled by lever 18 (FIG. 1) to wipe away debris from lens 43.

In the illustrated embodiment of FIGS. 1-3, the invention provides distribution of a preservative fluid in the region of V-keeper 14 so that, after a cauterizing event, the preservative fluid can be delivered to the target vessel proximate to the cauterized area. The fluid locally bathes the target vessel, not only resulting in cooling of the vessel but also minimizing the usual cascade of biochemical events that affect the endothelium even before the vessel is removed from the body. Since the fluid would interfere with cauterization, it is only delivered after cauterization is complete at each particular position along the length of the vessel.

As shown in FIGS. 2 and 3, a spray nozzle 50 receives preservation fluid via a fluid conduit 51 passing through frame 24 and rod 26. Nozzle 50 may be comprised of any suitable type of fluid exit with or without features for atomizing or otherwise dispersing an outflow of preservation fluid. By locating nozzle 50 on frame 25 (preferably oriented to spray fluid toward opening 28), the spray can be easily directed to a desired portion of the target vessel which is captured within opening 28. Thus, after V-cutter 15 has been energized to cauterize a side branch, V-keeper 14 is put into a position from which the preservative fluid spraying out from nozzle 50 will bathe the target vessel in an area proximate to where the cauterization has occurred. The preservative fluid may preferably be a biocompatible aqueous solution such as an isotonic saline solution. The saline solution may be lactated (such as with a lactated Ringer's solution) or may include medications (such as with a papaverine solution). Solutions other than saline can also be used, such as a potassium-chloride solution.

Figure 4:
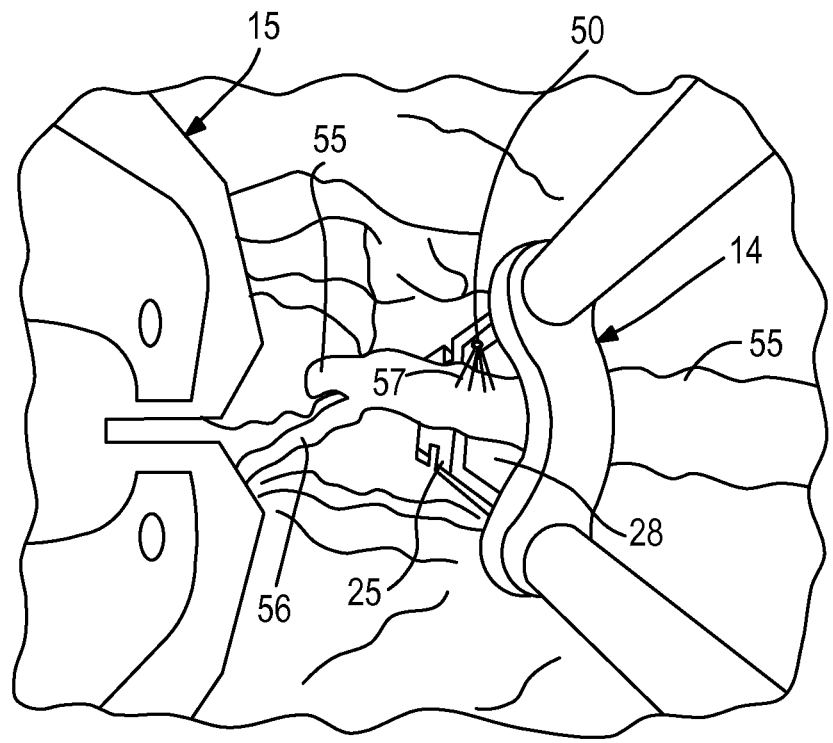
FIG. 4 is an endoscopic view of the harvester inside the body of a patient during harvesting of a vessel.

FIG. 4 is an endoscopic view as seen during vessel harvesting wherein a target vessel (e.g., saphenous vein) 55 is retained within opening 28 of V-keeper 14 within a cavity around vessel 55 created previously during blunt dissection. V-cutter 15 is in position for extending toward a side branch 56 for cauterizing and severing it to prepare a section of vessel 55 for removal. After cauterizing and severing branch 56, V-keeper frame 25 is positioned to align spray nozzle 50 alongside vessel 55 proximate to cauterized branch 56, and a supply of preservative fluid is activated in order to deliver a fluid spray 57. Besides a cooling effect provided by the fluid, preservation of the functioning of the endothelium is initiated much sooner than in the prior art which did not apply any preservative until the target vessel was removed from the body.

Figure 5:
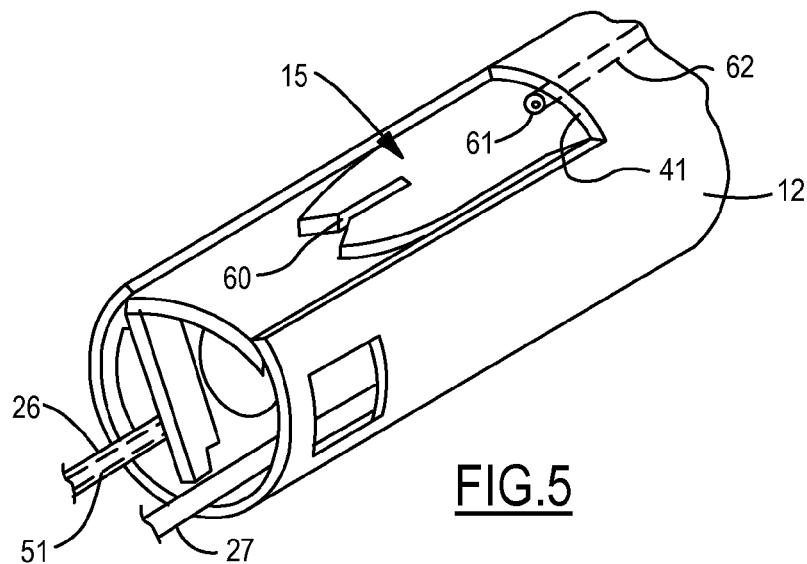
FIG. 5 is a perspective view of the cutter member and an irrigator for flushing debris from the cutter member.
Figure 6:
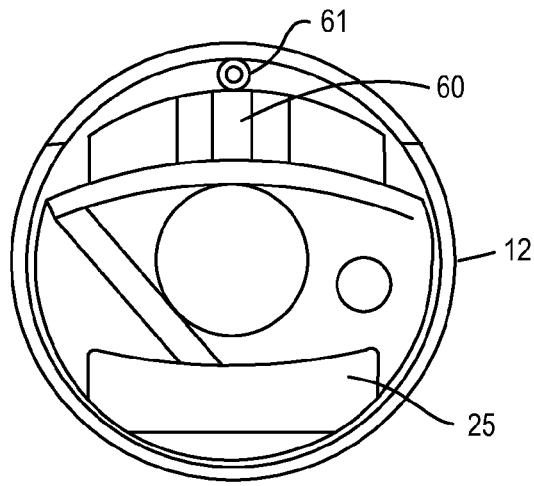
FIG. 6 is an end view of the embodiment of FIG. 5.

FIGS. 5 and 6 show a further embodiment of the invention wherein a fluid supply is simultaneously used within the harvester for the purpose of clearing debris from the V-cutter. Thus, an irrigator nozzle 61 is mounted to insertion member 12 at notch edge 41. Nozzle 61 is in longitudinal alignment with a slit 60 in V-cutter 15 for dispensing a fluid to clean slit 60 when V-cutter 15 is moved to the inward position. FIG. 6 shows an end view wherein nozzle 61 is located directly above slit 60. Preferably, nozzle 61 may be oriented to direct discharged fluid slightly downward in the figure.

Figure 7:
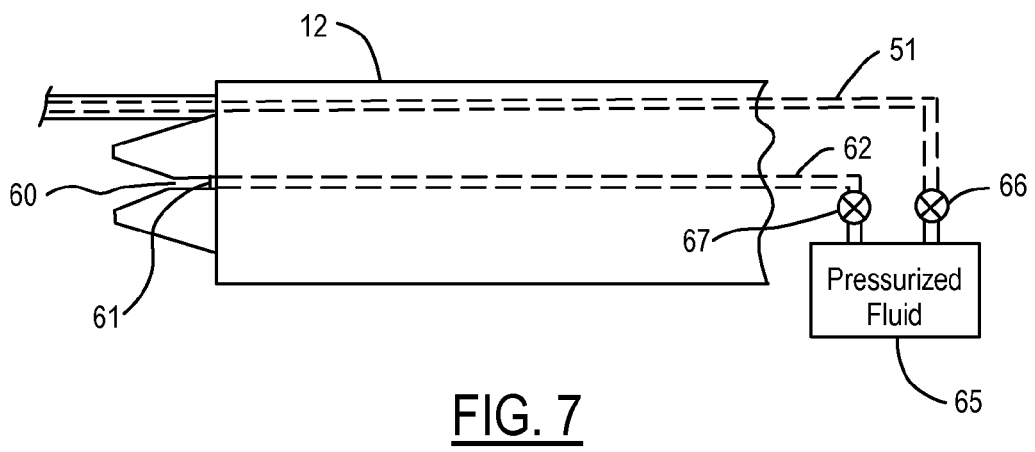
FIG. 7 is a block diagram showing the shared supply of preservative fluid for bathing the target vessel and flushing the cutter member.

FIG. 7 shows V-cutter 15 retracted to its inward position facilitating the flow of fluid in a jet from nozzle 61. A fluid distribution system is provided for sharing a supply of pressurized preservative fluid from a supply tank 65. Aqueous fluid is delivered to V-keeper spray nozzle 50 (FIGS. 2-4) by fluid conduit 51 passing through insertion member 12 from a first manually-controlled valve 66 which is connected to tank 65. In parallel, irrigation nozzle 60 receives the aqueous fluid via a fluid conduit 62 passing through insertion member 12. Conduit 62 selectably receives fluid via a second manually-controlled valve 67 connected to tank 65. Tank 65 may preferably include a pump (not shown) for outputting a flow of saline solution to selectably generate sprays from nozzles 50 and 61. The pump and valves 66 and 67 are operator controlled to coordinate creation of the spray with proper positioning of the V-keeper and/or the V-cutter.

During an endoscopic procedure to harvest a vessel, the endoscopic vessel harvester is inserted into the body alongside the vessel to be harvested. The cutter is extended and the electrodes are energized (e.g., by a foot pedal operated by a surgeon) to individually sever a plurality of branches. Periodically (e.g., after each cauterizing event), valve 66 is manually activated in order to bathe the target vessel with preservative fluid in the area proximate to the severed branch(es). Repeated cutting operations may result in a buildup of debris in the longitudinal slit. The cutter is then retracted to a position longitudinally inward from its cutting position while maintaining the endoscopic vessel harvester in the body so that the debris may be cleared from the longitudinal slit by manually activating valve 67 to deliver a spray that flushes away the debris.

What is claimed is:

1. An endoscopic vessel harvester comprising:
   a longitudinal insertion member having a proximal end with a handle and a distal end adapted for insertion into a tunnel dissected along a target vessel within a body of a patient;
   a vessel keeper extendably mounted at the distal end of the insertion member comprising a capture frame with a movable side having an opened position to admit the target vessel and having a closed position to slidably capture the target vessel;
   a cutter member extendably mounted at the distal end of the insertion member having a cauterizing element adapted to contact side branches of the target vessel and to cut and cauterize the side branches while the target vessel is slidably captured in the vessel keeper;
   a spray nozzle carried by the vessel keeper;
   a preservative distributor including a manual control valve and a conduit between the valve and the spray nozzle adapted to deliver a preservative fluid to the target vessel proximate a respective side branch immediately after being cauterized; and a support rod connected to the capture frame; wherein the conduit is carried within the support rod.

2. The harvester of claim 1 wherein the spray nozzle is attached to the capture frame.

3. The harvester of claim 1 wherein the support rod is slidably mounted in the insertion member and connected to the capture frame so that the support rod is manipulated at the handle to control extension of the vessel keeper.

4. The harvester of claim 1 further comprising a supply tank coupled to the conduit for storing the preservative fluid.

5. The harvester of claim 4 wherein the cutter member includes a slit into which the side branches are inserted for cutting, the harvester further comprising:
   an irrigator coupled to the supply tank via a second manual control valve adapted to selectably flush the slit with the preservative fluid.

6. The harvester of claim 4 wherein the supply tank is adapted to store a preservative fluid comprised of a biocompatible aqueous solution selected from an isotonic saline solution, a potassium-chloride solution, and a papaverine solution.

* * * * *